(12) United States Patent
Patil et al.

(10) Patent No.: US 12,186,725 B2
(45) Date of Patent: Jan. 7, 2025

(54) HIGH PRESSURE CARBAMATE CONDENSATION APPARATUS

(71) Applicant: Stamicarbon B.V., Sittard (NL)

(72) Inventors: Rahul Patil, Maastricht (NL); Lambertus Wilhelmus Gevers, Merelbeek (NL); Markus Theodorus Marie Michaël Wagemans, Roermond (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 18/578,192

(22) PCT Filed: May 12, 2023

(86) PCT No.: PCT/NL2023/050262
§ 371 (c)(1),
(2) Date: Jan. 10, 2024

(87) PCT Pub. No.: WO2023/219506
PCT Pub. Date: Nov. 16, 2023

(65) Prior Publication Data
US 2024/0261751 A1   Aug. 8, 2024

(30) Foreign Application Priority Data

May 13, 2022 (EP) .................................. 22173284

(51) Int. Cl.
*B01J 19/00* (2006.01)
*B01J 4/00* (2006.01)
*C07C 273/04* (2006.01)

(52) U.S. Cl.
CPC ........... *B01J 19/0013* (2013.01); *B01J 4/001* (2013.01); *B01J 19/006* (2013.01); *C07C 273/04* (2013.01); *B01J 2208/00176* (2013.01); *B01J 2208/00194* (2013.01); *B01J 2208/00256* (2013.01); *B01J 2219/00081* (2013.01)

(58) Field of Classification Search
CPC ...... B01J 19/0013; B01J 4/001; B01J 19/006; B01J 2208/00176; B01J 2208/00194; B01J 2208/00256; B01J 2219/00081; C07C 273/04
USPC ....................................................... 422/201
See application file for complete search history.

(56) References Cited

U.S. PATENT DOCUMENTS

| | | | |
|---|---|---|---|
| 5,767,313 | A | 6/1998 | Jonckers |
| 2015/0086440 | A1 | 3/2015 | Scheerder |

(Continued)

FOREIGN PATENT DOCUMENTS

| | | |
|---|---|---|
| DE | 3024819 | 1/1982 |
| ES | 2440088 | 1/2014 |
| WO | 9500674 | 1/1995 |

(Continued)

OTHER PUBLICATIONS

Machine translation of DE-3024819 A1 (Year: 2024).*

(Continued)

*Primary Examiner* — Huy Tram Nguyen
(74) *Attorney, Agent, or Firm* — Leason Ellis LLP

(57) ABSTRACT

The disclosure pertains to a high pressure carbamate condensation apparatus for a urea plant, a urea plant, and a urea production method. The apparatus comprises a first U-shaped tube bundle arranged around a second U-shaped tube bundle.

18 Claims, 2 Drawing Sheets

(56) References Cited

U.S. PATENT DOCUMENTS

2015/0119603 A1    4/2015  Van Den et al.
2020/0306663 A1   10/2020  Poppa

FOREIGN PATENT DOCUMENTS

WO    2017014632    1/2017
WO    2019083367    5/2019

OTHER PUBLICATIONS

Massimo Gori et al, "Stamicarbon's Ultra Low Energy Design", ureaknowhow.com, Feb. 26, 2018, blz 263-269.
International Search Report for corresponding International Application No. PCT/NL2023/050262, dated Aug. 16, 2023 (3 pages).
Gori Massimo et al: "Stamicarbon's Ultra Low Energy Design Author", Feb. 26, 2018 (Feb. 26, 2018), pp. 263-269, XP055973121, Gothenburg Retrieved from the Internet: URL:https://ureaknowhow.com/wp-content/uploads/2018/09/2018-GoriStamicarbon-Ultra-Low-Energy-Design.pdf [retrieved on Oct. 20, 2022].
Power HX Tech CO LTD http://www.powerhx.com/eng/product/exchanger.php, 2017.
Jo Meessen, The Stamicarbon low energy urea melt plant, conference paper, Renewable Energy in Fertilizer Industries & Energy Auditing, Apr. 28-30, 2013.
Stamicarbon's Ultra Low Energy Design; Technical Paper, Sep. 2018.
Meessen, "Urea", Ullmann's Encyclopedia of Industrial Chemistry, Chapter Urea, 2010, pp. 1-39.

* cited by examiner

HIGH PRESSURE CARBAMATE CONDENSATION APPARATUS

CROSS-REFERENCE TO RELATED PATENT APPLICATIONS

This application is a U.S. National Stage Application under 35 U.S.C. § 371 of International Patent Application No. PCT/NL2023/050262, filed May 12, 2023, which claims the benefit of priority of European Patent Application No. 22173284.5, filed May 13, 2022, both of which are incorporated by reference in their entireties. The International Application was published on Nov. 16, 2023, as International Publication No. WO/2023/219506 A1.

FIELD

The invention pertains to the production of urea from $CO_2$ and $NH_3$.

INTRODUCTION

Example urea production plants are illustrated in Ullmann's Encyclopedia of Industrial Chemistry, Chapter Urea, 2010.

US 2015/0119603A1 describes a urea production plant with a high pressure synthesis section with a horizontal pool condenser configured to receive a high pressure process medium at a shell side thereof, wherein the pool condenser comprises a first tube bundle receiving medium pressure urea solution and a second tube bundle receiving steam condensate. Both tube bundles are illustrated as vertically stacked horizontal U-shaped tube bundles. As illustrated, the urea solution is supplied to the bottom straight tube parts of the lower tube bundle.

US 2020/0306663A1 describes a high pressure carbamate condenser of the shell-and-tube heat exchanger type with a tube bundle which has a redistribution chamber connected to tubes of the tube bundle and to a duct that extends between the redistribution chamber and the shell. FIG. 3 of US'663 shows a high pressure carbamate condenser with two U-shaped tube bundles wherein the lower tube bundle receives urea solution at the lower leg portion.

The brochure "Stamicarbon's Ultra Low Energy Design; Technical Paper", September 2018, shows a pool condenser/reactor with two stacked U-shaped tube bundles with urea solution supplied to the bottom tube bundle.

There remains a desire for an improved high pressure (HP) carbamate condensation apparatus for urea plants, in particular with improved heat exchange properties.

SUMMARY

The invention pertains in a first aspect to a high pressure carbamate condensation apparatus comprising a shell-and-tube heat exchanger comprising a shell and a first and a second horizontal U-shaped tube bundle each having an upper leg portion and a lower leg portion connected by a bend portion, a shell side space confined by the shell, a first fluid distributor arranged in the shell side space at a bottom section of the condensation apparatus for distributing a first high pressure gas stream into the shell side space, and an inlet and an outlet for a medium pressure (MP) urea-comprising stream, wherein the first U-shaped tube bundle is arranged around the second U-shaped tube bundle and the upper leg portion of the outer first U-shaped tube bundle is proximally connected to the inlet for the MP urea-compris- ing stream and the lower leg portion of the outer first U-shaped tube bundle is proximally connected to the outlet for the MP urea-comprising stream and wherein the inner second U-shaped tube bundle is configured for raising steam.

The invention also pertains to a urea production plant comprising a high pressure synthesis section comprising a HP stripper, a reaction zone, and a high pressure carbamate condensation apparatus according to the invention. The high pressure synthesis section has a liquid flow connection for urea solution through an expansion device to said inlet for MP urea-comprising stream and to said upper leg portion of the outer first U-shaped tube bundle. The HP stripper has a gas flow line connected to a gas inlet of the shell side of the condensation apparatus.

The invention also pertains to a urea production process for the production of urea from ammonia and carbon dioxide carried out in a urea production plant according to the invention, the process comprising supplying gas from the HP stripper to the shell side of the HP carbamate condensation apparatus and condensing said gas into carbamate at least in part at said shell side and converting said carbamate at least in part into urea at said shell side, and supplying an MP urea solution also comprising carbamate to said inlet for an MP urea-comprising stream.

Aspects of the invention hence pertain to a high pressure carbamate condensation apparatus for a urea plant, a urea plant, and a urea production method. The apparatus comprises a first U-shaped tube bundle arranged around a second U-shaped tube bundle.

Figure 1:
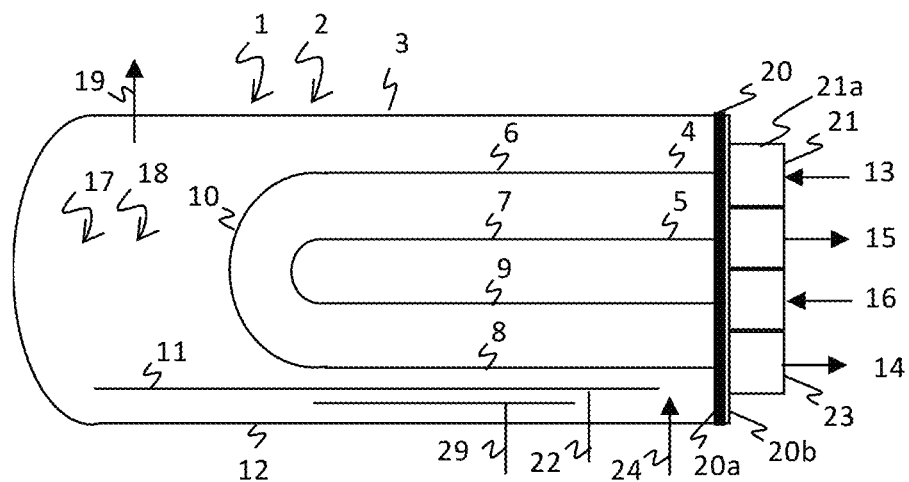
FIG. 1 schematically illustrates an example of a HP carbamate condensation apparatus according to the invention.

Any embodiments illustrated in the figures are examples only and do not limit the invention.

DETAILED DESCRIPTION

An aspect of the invention is directed to a HP horizontal carbamate condensation apparatus of the shell-and-tube heat exchanging type. The apparatus is in particular a horizontal submerged condenser. Two examples of such a horizontal submerged condenser which can be used in the present invention but which do not limit the invention, are a pool condenser and a pool reactor.

A submerged condenser is a condenser wherein in operation the tube bundles are submerged in liquid process medium present in the shell side space. The inventive apparatus comprises a shell side space between the shell (wall) and the tubes. The shell side space is in operation filled with HP process medium. The gas from the HP stripper comprising $NH_3$ and $CO_2$ is condensed into carbamate-containing solution in the shell side space and cooling fluid passes through the tubes in operation. Gas to be condensed is supplied and distributed by one or more gas distributors at the bottom of the shell side space.

The invention is, in an aspect, based on the judicious insight that the heat exchanging properties of the HP carbamate condensation apparatus can be improved by benefitting from the cross-flow effect between medium pressure (MP) urea solution in the tubes of a U-shaped tube bundle and condensing process medium in the shell side space. Process medium in the shell side space flows up between the tubes of the tube bundles and MP urea solution comprising carbamate used as cooling fluid flows inside the tubes from an upper leg part of the horizontal tube bundle to a lower leg part of the horizontal tube bundle and increases in temperature, such that the relatively cold urea solution in the upper leg part is in heat exchanging contact with the relatively colder process medium in the upper part of the shell side space. This contributes to optimum heat exchange and thereby advantageously the heat exchanging surface can be smaller.

In particular, as the carbamate condensation reaction is fast and exothermic and the urea formation reaction already at least in part occurs in the condensation apparatus and is endothermic and relatively slow, the configuration of the first and second tube bundle according to the invention allows for good heat exchange between the cooling fluid in the tubes and the process medium (in the shell side space), taking into account the vertical temperature profile of the process medium on the shell side and taking into account the temperature profile of the urea solution flowing through the first U-shaped tube bundle.

An aspect of the invention pertains to a HP carbamate condensation apparatus, in particular for a urea plant. The apparatus may be a submerged condenser, for instance a pool condenser or a pool reactor. The apparatus is discussed with reference to FIG. 1, which figure however does not limit the invention or the claims.

The HP carbamate condensation apparatus (1) comprises a shell-and-tube heat exchanger (2) which comprises a shell (3) and a first and a second horizontal U-shaped tube bundle (4, 5). The heat exchanger hence has a tube side and a shell side.

With respect to the HP carbamate condensation apparatus (1), the horizontal direction is defined by the legs of the tubes (4, 5), the legs are horizontally arranged. Additionally, the length direction is defined by the legs of the tubes (4, 5), which are arranged in the length direction. The bottom section of the HP carbamate condensation apparatus (1) is defined by the first fluid distributor (11). For the urea plant, vertical is defined with respect to gravity and the HP carbamate condensation apparatus (1) is arranged accordingly.

The shell (3) confines the shell side space (18). The shell is for instance a vessel having a horizontal length direction; preferably a cylindrical vessel. The shell is for instance at one end capped with a cap, e.g. a substantially hemispherical cap part, and at another end closed by a tube sheet, or is for instance at two ends capped with a cap. The cap and tube sheet, or the two caps, delimit the shell side space (18) and are at the internal side exposed to HP process medium in the shell side space (18).

The parts of the carbamate condensation apparatus (1) that are in contact with the process medium, especially at higher temperature (for example the process medium condensing at high pressure in the condenser) are typically made of corrosion resistant materials, in particular urea grade steel, such as an austenitic-ferritic duplex stainless steel (duplex steel). For instance, the shell is at the inside provided with overlay welding (i.e. a weld overlay) or internal lining made of urea grade steel or other corrosion resistant metal, e.g. duplex austenitic-ferritic stainless steel, AISI 316L steel, or INOX 25/22/2 Cr/Ni/Mo steel. Such internal lining is typical for the shell of a HP carbamate condensation apparatus (1). The outside shell is e.g. a carbon steel shell and is e.g. at least 30 mm or at least 40 mm thick.

The HP carbamate condensation apparatus (1) further comprises a first fluid distributor (11). The first fluid distributor (11) is arranged in the shell (3) at a bottom section (12) of the condensation apparatus (1). The first fluid distributor (11) is used for distributing a first high pressure gas stream, in particular from the HP stripper, at the shell side, i.e. in the shell side space (18). The first HP gas stream may be supercritical. The first fluid distributor is in particular arranged horizontally, for horizontally distributing the gas stream.

The first fluid distributor (11) is for instance a sparger. A sparger for instance comprises a tube extending in the length of the shell, wherein said tube is provided with arms extending in the width direction at both sides of the tube. The arms are spaced apart in the length direction. The arms have numerous outlet openings for gas (e.g. more than 50 openings per arm) at the upper side of the arms. A sparger may comprise two or more of such tubes with arms. Generally, the first fluid distributor is provided with an upper surface containing a large number (e.g. more than 50) outlet openings for gas which are distributed in the length and width direction.

The first fluid distributor (11) is connected to a gas inlet (22) comprised in the shell (3); the gas inlet is configured to supply gas to be condensed into shell side space (18).

The first fluid distributor (11) and the straight parts (legs) of the tubes of the tube bundles extend in parallel in the length direction of the shell (3). The arms extend horizontally over the width direction, i.e. perpendicular to the length direction.

The first fluid distributor (11) is typically configured for distributing the gas over the width of the tube bundles (4, 5) and at least over the length of the tube bundles (4, 5); preferably the tube bundles (4, 5) have the same width and the leg parts of the first and second U-shaped tube bundle (4, 5) have the same length. The shell (3) is wider than the tube bundles (4, 5) and permits for downward fluid flow in the shell side space around the tube bundles (4, 5).

The shell side (18) of the HP carbamate condensation apparatus (1) furthermore typically comprises a carbamate inlet (24) for receiving recycle carbamate solution from one or more recovery sections that are used to purify urea solution from the HP synthesis section.

The shell (3) furthermore comprises an outlet (19) for process fluid for withdrawing process fluid from the shell side space (18). The process fluid comprises a solution comprising urea and carbamate.

In some embodiments, the shell side space (18) is completely filled with process fluid in operation and the process fluid at the outlet (19) includes both gas and liquid. The process fluid is e.g. supplied to a gas/liquid separation unit external of the condensation apparatus. The outlet (19) is arranged at a top side of the shell (3) in such embodiments.

In some embodiments, a liquid level is maintained in the shell side space (18) in operation and the condensation apparatus comprises a liquid overflow element in the shell side space (18), such as a baffle or a downcomer. The overflow element may act as a weir.

In operation, the entire first and the second tube bundle (4, 5) are submerged by and in the liquid phase in the shell side space (18). Hence, the HP carbamate condensation apparatus (1) provides a horizontal submerged carbamate condenser.

The HP carbamate condensation apparatus (1) comprises an inlet (13) and an outlet (14) for MP urea-comprising stream, i.e. for a fluid stream comprising a liquid phase comprising urea. The liquid phase also comprises carbamate at least at the inlet (13) and typically also, but less, at the outlet (14). The fluid stream also comprises gas, at least at the outlet (14) due to decomposition of at least part of the carbamate during the passage of the fluid through the first U-shaped tube bundle (4). The fluid is at a pressure in the medium pressure (MP) range at the inlet and the outlet.

The MP urea-comprising stream inlet (13) and outlet (14) are both connected to the first U-shaped tube bundle (4).

The MP urea-comprising stream inlet (13) and outlet (14) are provided in an external wall (23) of the HP carbamate condensation apparatus (1). The external wall (23) is typically exposed to the outside environment in a urea plant. The external wall (23) may be provided, for example, by the shell (3) or by an additional element of the apparatus, such as a header (21) located outside of the shell (3).

The inlet (13) and the outlet (14) are both provided with connecting means, such as flanges, for coupling to a fluid flow line of the plant for the MP urea stream, e.g. to piping.

The inlet (13) and outlet (14) are both connected to the first U-shaped tube bundle (4) through a respective connection chamber which connects the inlet respectively outlet to the large number of tubes of the tube bundle. The connection chamber is e.g. a header (21) formed in part by the tube sheet (20), or is for example a redistribution chamber located inside the shell side space, for example a redistribution chamber as described in more detail and as described in US 2020/0306663A1.

FIG. 1 illustrates an example embodiment wherein the condensation apparatus comprises a tube sheet (20) and the connection chamber (21a) is provided as a header (21). In such an embodiment with a tube sheet (20), the tube sheet (20) is preferably also provided with a corrosion-resistant layer, e.g. duplex stainless steel layer, e.g. provided with overlay welding, on the side exposed to the header (21), in particular because the header comprises MP urea solution comprising carbamate in operation.

Generally, if used, the tube sheet (20) has an opening for each end of each U-shaped tube of the tube bundle (4, 5), e.g. the tube ends extend through an opening (bore hole) of the tube sheet (20) or a sleeve extends from the tube through the opening. Examples of sleeves extending through bore holes of the tube sheet are described in US 2015/0086440.

Generally, if used, the tube sheet (20) comprises e.g. a carbon steel plate and a layer with a corrosion resistant material, in particular urea grade steel, on the side exposed to the shell side space (18). Preferences for the material of the layer are the same as for the internal lining of the shell (3). The layer is e.g. provided with overlay welding.

Hence, preferably, the condensation apparatus (1) comprises a tube sheet (20), wherein the tube bundles (4, 5) are arranged at a first side (20a) of said tube sheet (20) and said inlet (13) and outlet (14) for MP urea-comprising stream are provided by headers (21) arranged at a second side (20b) of said tube sheet (20). The first side (20a) is facing the shell side space (18) and is hence exposed to the shell side space (18). The second side (20b) of the tube sheet (20) is external and is not exposed to the shell side space (18). The tube sheet (20) seals off the shell (3) and the shell side space (18).

Generally, the first U-shaped tube bundle (4) has an inlet end and an outlet and. Typically all tube ends of the inlet end are directly connected to a single inlet connection chamber (21a) which in turn is connected to the inlet (13) for the MP urea stream. Typically all tube ends of the outlet end are directly connected to a single outlet connection chamber which in turn is connected to the outlet (14) for the MP urea stream.

The tube bundles each have an upper leg portion (6,7) and a lower leg portion (8,9) connected by a bend (10). Each tube of the tube bundle comprises two horizontal legs connected by a bend. The legs of the tubes are arranged in parallel in a tube bundle in the length direction of the shell (3). The upper and lower leg of a tube are vertically spaced apart and are connected by the bent part of the U-shaped tube.

The total number of tubes in the tube bundles is e.g. at least 50 or at least 100 or at least 500. The first and the second tube (4, 5) bundle for instance comprise at least 100 tubes each. The number of tubes depends on plant capacity.

In the invention, the first U-shaped tube bundle (4) is arranged, e.g. looped, around the second U-shaped tube bundle (5), i.e. the first U-shaped tube bundle (4) is arranged concentrically around the second U-shaped tube bundle (5). The bends of the first tube bundle are hence preferably concentric with the bends of the second U-shaped tube bundle (5). The first U-shaped tube bundle (4) is the outer tube bundle and is arranged the closest to the shell. The second U-shaped tube bundle (5) is typically at least partially enveloped by the outer first U-shaped tube bundle.

The upper leg portion (6) of the outer first U-shaped tube bundle (4) is proximally connected to the inlet (13) for the MP urea-comprising stream. The lower leg portion (8) of the outer first U-shaped tube bundle (4) is proximally connected to the outlet (14) for the MP urea-comprising stream.

Herein, proximally connected indicates in particular a connection for fluid flow between the leg portion and the inlet respectively outlet without passing through the bend portion (10) of the tubes.

In particular, the condensation apparatus comprises a connection chamber (21a) that is directly connected to the upper leg portion (6) of the outer first U-shaped tube bundle (4) and connected, optionally through a duct, to the inlet (13) for the MP urea-comprising stream. The connection chamber (21a) is for example a header (21) as shown in present FIG. 1 used in combination with a tube sheet (20). Such a header is also shown in FIG. 1 of US 2020/0306663A1. The connection chamber can also be provided by a redistribution chamber and duct, for example as shown in FIG. 2A of US 2020/0306663A1.

Preferably the lower leg portion (8) of the outer first U-shaped tube bundle (4) is directly connected to a connection chamber (21a) that is connected, optionally through a duct, to the outlet (14) for the MP urea-comprising stream Preferably the upper leg portion (7) of the inner second U-shaped tube bundle (5) is proximally connected to an outlet for steam (15) and the lower leg portion (9) of the inner second U-shaped tube bundle (5) is proximally connected to an inlet for boiler feed water (16); again preferably through a connection chamber (21a).

The inner second U-shaped tube bundle (5) is configured for raising steam, in particular is connected to an inlet for boiler feed water (16) and an outlet (15) for steam. The outlet (15) is for instance connected to a steam drum. The inlet for boiler feed water (16) is for instance connected to a steam condensate tank which comprises e.g. a condensation unit. The boiler feed water is for instance steam condensate. The boiler feed water at the inlet (16) is for instance at 4-5 bar gauge. The fluid at the outlet (15) comprises steam and optionally condensate (wet steam). The fluid at the outlet (15) is e.g. 3.5-4.5 bar gauge steam.

Preferably the outlet (14) for the MP urea-comprising stream has a larger flow area than the inlet (13) for the MP urea-comprising stream, preferably at least 1.1 or at least 1.2 times larger. Thereby the condensation apparatus is adapted for carbamate dissociation in the first U-shaped tube bundle giving two-phase fluid flow at the outlet (14).

Optionally the outlet (14) for the MP urea-comprising stream is provided by two or more outlet nozzles and the total flow area of these outlet nozzles is larger than that of the inlet. The flow area of the individual nozzles may be smaller than that of the inlet.

Optionally the inlet (13) for the MP urea-comprising stream is provided by two or more inlet nozzles.

Preferably the condensation apparatus, more preferably the vessel, comprises a reaction zone (17) in the shell (3), i.e. in the shell side space (18), between the bend (10) of the first U-shaped tube bundle (4) and the shell (3). The reaction zone extends (17) over e.g. at least 10% or at least 20% and/or up to 60% of the length of the vessel and shell (3). The reaction zone (17) has a size in the length direction of the shell (3) of e.g. at least 20% or at least 50% or e.g. at least 60% and or up to 150% of the length of the straight parts (individual leg) of the outer first U-shaped tube bundle (4).

This reaction zone (17) allows for the carbamate dehydration reaction to take place. Preferably the first fluid distributor (11) extends at the bottom of the reaction zone (17). This contributes to maintaining the heat balance in the reaction zone. Accordingly, in a preferred embodiment the condensation apparatus is a pool reactor.

In particular, preferably the U-shaped horizontal tube bundles (4, 5) extend over less than 80% or less than 70% of the horizontal length of the shell (3), or of the shell side space (18), and the remaining part of the shell side space (18) provides for said reaction zone (17) in the shell side space (18). Thereby the carbamate condenser and the reaction zone (17) are provided by a single vessel, which can be referred to as a pool reactor. The pool reactor preferably comprises baffles in the shell (3). Preferably one of the baffles is configured as an overflow weir providing for gas/liquid separation in the shell side space (18). Preferably the shell side space (18) has a liquid outlet and a separate outlet for gas (not shown in FIG. 1, shown in FIG. 2). In operation, urea formation already takes place in the shell side space (18); in particular the reaction zone (17) may provide for sufficient residence time of liquid for the urea formation reaction. Urea solution from the shell side space (18) of the pool reactor is supplied e.g. directly to the HP stripper.

Preferably the condensation apparatus, more preferably the vessel, comprises a second fluid distributor, in particular a sparger, arranged at a bottom section of the condensation apparatus for distributing a second high pressure gas stream, in particular $NH_3$, more in particular $NH_3$ feed, at the shell side (3), in particular into the shell side space (18). Preferably the second fluid distributor extends horizontally, below the first tube bundle (4), and preferably is coterminous with the bend (10) of the first tube bundle (4). If a reaction zone (17) is present, the second fluid distributor, in particular the $NH_3$ sparger, preferably does not extend into the reaction zone. The $NH_3$ sparger is connected to an inlet for $NH_3$ in the shell. The optional $NH_3$ sparger (29) is illustrated in FIG. 1.

In a preferred embodiment the apparatus (1) comprises a redistribution chamber, preferably located in the shell side space (18), wherein said redistribution chamber comprises a wall for separating HP process medium in the shell side from MP urea stream inside the redistribution chamber, wherein an end of the first U-shaped tube bundle (4) is connected to the redistribution chamber such that said MP urea stream can flow between the first U-shaped tube bundle (4) and said redistribution chamber. Preferably the condensation apparatus further comprises a duct extending from the inlet (13) or the outlet (14) for the MP urea stream to said redistribution chamber, such that the MP urea stream can flow between the first tube bundle (4) and said inlet (13) or outlet (14) through said redistribution chamber and said duct. Preferably, the apparatus comprises four redistribution chambers, one for each end of the first and second U-shaped tube bundle (4, 5); each redistribution chamber having a respective duct to an inlet or outlet in the shell (3). In this embodiment, the tube sheet (20) can be omitted. The redistribution chamber is spaced apart from the shell (3). The duct is in operation surrounded by HP process medium in the shell side space (18).

Preferably the duct of the redistribution chamber that is connected directly to the upper leg portion (6) of the outer first U-shaped tube bundle (4) is arranged vertically upward, i.e. vertically and with the duct part extending through the shell spaced further from the horizontal first fluid distributor (11) than the joint between the duct and that redistribution chamber. This vertical arrangement of this duct contributes to good distribution of the MP urea solution from the inlet (13) to the numerous tubes of the first U-shaped tube bundle (4).

The redistribution chamber is preferably made of duplex stainless steel, more preferably of single sheet plate elements of duplex stainless steel. The tube ends can protrude through bore holes of a wall, e.g. plate, of the redistribution chamber into the tube, using welding at the internal side of the chamber. Crevice corrosion can be avoided or mitigated by using duplex stainless steel as construction material for the redistribution chamber wall.

Further details and preferences of the duct and the redistribution chamber are given in US 2020/0306663A1.

For all elements that are preferably made of duplex stainless steel, a particularly preferred duplex stainless steel alloy is the steel available as Safurex® steel and having composition 29Cr-6.5Ni-2Mo-N, which is also designated by ASME Case 2295-3 and by UNS S32906. The duplex stainless steel has for instance the composition (% by mass): C: max. 0.05, Si: max. 0.8, Mn: 0.3-4.0, Cr: 28-35, Ni: 3-10, Mo: 1.0-4.0, N: 0.2-0.6, Cu: max. 1.0 W: max. 2.0 S: max. 0.01 Ce: 0-0.2, balance Fe and (unavoidable) impurities. Preferably the ferrite content is 30-70% by volume and more preferably 30-55%. More preferably, the steel contains (% by weight): C max. 0.02, max. 0.5 Si, Cr 29 to 33, Mo 1.0 to 2.0, N 0.36 to 0.55, Mn 0.3 to 1.0, balance Fe and unavoidable impurities. Example steels are specified in as described in WO 95/000674 herein incorporated by reference. Also suitable is a duplex stainless steel having the composition weight % (wt. %): C max 0.030; Si max 0.8; Mn max 2.0; Cr 29.0 to 31.0; Ni 5.0 to 9.0; Mo less than 4.0; W less than 4.0; N 0.25-0.45; Cu max 2.0; S max 0.02; P max 0.03; balance Fe and unavoidable occurring impurities; and wherein the content of Mo+W is greater than 3.0 but less than 5.0 (wt. %), furthermore preferably with a steel composition as described in WO 2017/014632 hereby incorporated by reference. Also possible is the steel available as and steel available as DP28W™ steel and having composition 27Cr-7.6Ni-1 Mo-2.3W—N, which is also designated by ASME Case 2496-1 and by UNS S32808.

The invention also pertains to a urea production plant comprising the HP carbamate condensation apparatus (1) according to the invention.

Figure 2:
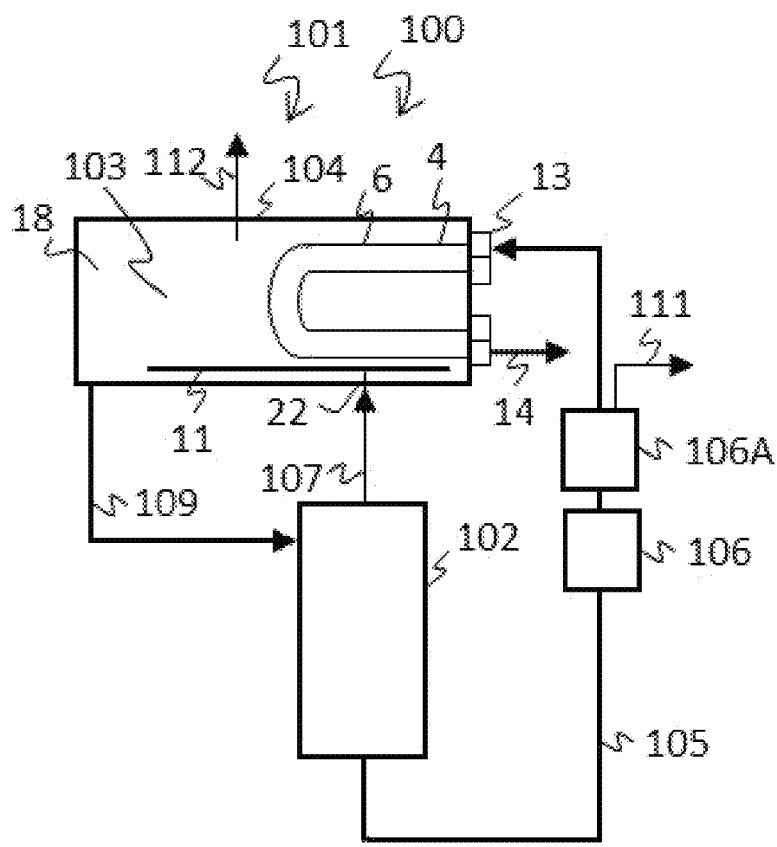
FIG. 2 schematically illustrates an example urea production plant according to the invention.

With reference to the non-limiting example embodiment of FIG. 2, the urea production plant (100) in particular comprises a HP synthesis section (101) comprising HP stripper, preferably a $CO_2$ HP stripper (102), a reaction zone (103), and the HP carbamate condensation apparatus (104) according to the invention. The HP synthesis section (101), e.g. the HP stripper (102), has a liquid flow connection (105) for urea solution through an expansion device (106) to the inlet (13) for MP urea-comprising stream and in particular to the upper leg portion (6) of the outer first U-shaped tube bundle (4). A two-phase fluid flow (gas/liquid) is formed by the expansion from HP to MP in expansion device (106). A gas/liquid separation unit (106A) is provided downstream of the expansion device (106), and has a liquid outlet connected to the inlet (13) and an outlet (111) for gas.

The stripper (102) receives urea synthesis solution (109) from the reaction zone (103) and has a gas outlet at the top. In case the HP stripper (102) is a $CO_2$ stripper, the stripper has an inlet for $CO_2$ at the bottom (not shown).

Preferably the shell side space (18) of the HP carbamate condensation apparatus (104) has a liquid outlet (109) for urea solution and a separate outlet (112) for gas.

The HP synthesis section (101) also has an inlet for $NH_3$ feed (not shown), such as to the HP carbamate condensation apparatus (104).

The plant comprises a gas flow line (107) from the HP stripper gas outlet to a gas inlet (22) of the shell side of the condensation apparatus (104). In FIG. 2, further reference numerals are the same as for FIG. 1.

The HP stripper (102), is preferably the $CO_2$ stripping type. Alternatively the HP stripper (102) can be of the thermal stripping type.

The HP stripper (102) is a vertical shell-and-tube heat exchanger with in operation a falling film of urea solution to be stripped in the tubes and heating medium, in particular steam, in the shell, having a liquid inlet and gas outlet at the top and a liquid outlet for stripped urea solution at the bottom, and preferably also having an inlet for $CO_2$ feed used as strip gas at the bottom. The gas outlet of the stripper is connected to a gas inlet of the shell side of the HP carbamate condensation apparatus (104). The liquid inlet is connected to the reaction zone (103) to receive all or a part of the liquid from the reaction zone.

In embodiments with a $CO_2$ HP stripper (102), the N/C ratio of the urea solution at the reaction zone (103) (or reactor) outlet is e.g. 2.8-3.8, e.g. 2.9-3.2. Preferably the synthesis pressure is in the range of 140-150 bar in the synthesis section. Preferably the reaction zone (103) (e.g. reactor), condenser (104) and stripper (102) form a substantially isobaric loop.

The N/C ratio ($NH_3:CO_2$ ratio) of the reaction zone (103) reflects the composition of the so-called initial mixture before urea production, consisting only of $NH_3$, $CO_2$ and $H_2O$, as used in the art of urea plants, and is the molar ratio, and is measured at the outlet of the reaction zone (103) for urea synthesis solution.

The HP synthesis section (101), in particular the reaction zone (103) and/or the HP stripper (102), has a liquid flow connection for HP urea solution through an expansion device (106), e.g. a control valve, to the inlet (13) for MP urea-comprising stream and to the outer first U-shaped tube bundle (4), and in the invention in particular to the upper leg portion (6) of the first U-shaped tube bundle (4).

The urea production plant (100) preferably also comprises a gas/liquid separation unit (106A) directly downstream of the expansion device (106), which unit is e.g. a flash vessel, more preferably an MP adiabatic flash vessel.

The HP synthesis section (101) comprises a reaction zone (103). The reaction zone (103) is typically provided as a vertical urea reactor or as a part of said HP carbamate condensation apparatus (100). Two or more reaction zones may be provided in parallel or in series.

The HP synthesis section (101) comprise one or more inlets for $CO_2$ feed and for $NH_3$ feed; wherein at least a part of the $CO_2$ feed is used as strip gas in the HP stripper (102).

In an embodiment, the HP synthesis section (101) comprises a pool reactor and a stripper (102). In a further embodiment, the HP synthesis section (101) comprises a pool condenser, a vertical urea reactor, and a stripper (102). In yet a further embodiment, the HP synthesis section (101) comprises a pool reactor, and a vertical reactor as after reactor, and a stripper (102). The vertical urea reactor typically has an inlet at the bottom, an outlet for withdrawing urea solution from the top section, optionally using a downcomer, and comprises trays.

In a preferred embodiment, the urea production plant (100) comprises a gas/liquid separator (106A), e.g. a flash vessel, that is connected to receive urea solution from the expansion device (106), in particular to receive two-phase fluid comprising urea solution. The gas/liquid separator (106A) is arranged at a vertically higher level of the plant than the inlet for MP urea-comprising stream (13) and the upper leg portion (6) of the outer first U-shaped tube bundle (4), preferably at least 2 m or at least 4 m higher. For vertical levels of the plant, vertical is defined with respect to gravity. The gas/liquid separator (106A) has a liquid outlet connected to the inlet (13) for MP urea-comprising stream; and a separate gas outlet (111), and a separate inlet connected to said expansion device (106).

Preferably a urea solution liquid column of at least 3 m height, or at least 6 m height, is maintained at the inlet (13) for the MP urea-comprising stream. Preferably in the urea production process a liquid column of urea solution e.g. at least 2 or at least 4 m height, and/or e.g. up to 12 m or up to 10 m height, is maintained between the liquid outlet of the gas/liquid separator (106) and the inlet (13), in particular the upper legs (6). This liquid column height and corresponding pressure head at the inlet (13) provides for gravity flow of the urea solution through the tubes. The pressure head also improves liquid distribution over the tubes.

Preferably the expansion device (106) where the urea synthesis solution is expanded from HP to MP is located at ground level of the urea production plant (100). Preferably the solution is stripped urea solution from a HP stripper (102) located at ground level. Herein, "ground level" of a plant indicates up to 7 m above ground level. Placing the expansion device (106) (e.g. HP control valve) directly on ground level is preferred.

Thereby advantageously mechanical energy released by the expansion of urea solution from HP to MP, i.e. the pressure reduction of e.g. at least 50 bar or at least 70 bar can be used for transporting the liquid to a higher level, in particular to the inlet of the gas/liquid separator (106), which is arranged e.g. at 25 m to 50 m higher than the HP control valve.

Figure 3:
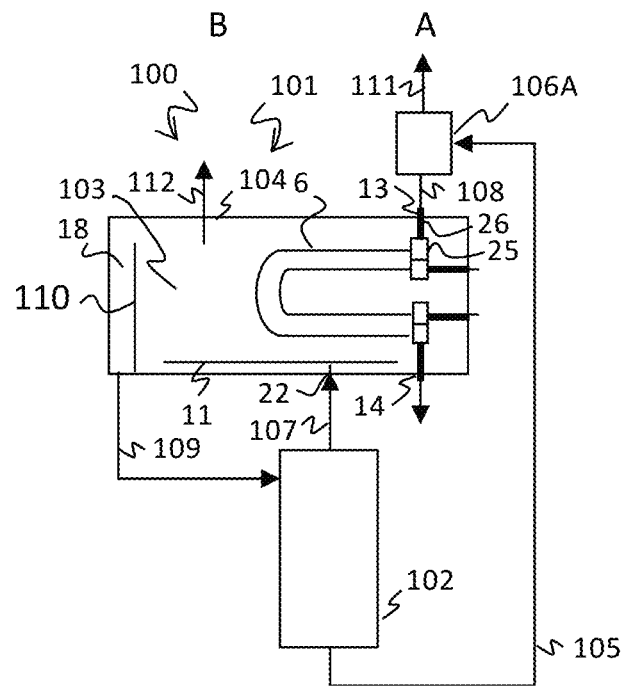
FIG. 3 schematically illustrates an example urea production plant according to the invention.

FIG. 3 schematically illustrates an example HP condensation apparatus and plant according to the invention. Reference numbers are the same as in FIG. 2 unless otherwise specified. The HP carbamate condensation apparatus (104) comprises a redistribution chamber (25) located in the shell side space (18) and spaced apart from the shell (3). The wall of the redistribution chamber (25) is at the outside in contact with HP process medium and at the inside with MP urea solution. The redistribution chamber (25) is connected to the inlet (13) for MP urea-comprising stream located in the shell (3) by the duct (26). The HP carbamate condensation apparatus (104) contains four redistribution chambers (25) each connected by a duct (26) to an inlet or outlet in the shell (3).

As an independent feature, the urea production plant (100) of FIG. 3 also comprises a gas/liquid separator (106A), e.g. a flash vessel, receiving urea solution from the expansion device (106). The flash vessel (106A) is arranged at a vertically higher level of the plant than the inlet (13) for MP urea-comprising stream and the upper leg portion (6) of the outer first U-shaped tube bundle (4), e.g. 4-8 m above the upper leg portion (6). The flash vessel has a liquid outlet (108) at the bottom that is connected to the inlet (13) for MP urea-comprising stream; and a separate gas outlet (111) at the top. This arrangement of the flash vessel (106A) can also be used in combination with the tube sheet (20).

In the embodiment illustrated in FIG. 3, the liquid outlet (108) is connected directly to the inlet (13). In particular no pressure reducing element, such as a control valve, is present between the liquid outlet (108) and the inlet (13) of the outer first U-shaped tube bundle (4). The static pressure at the inlet (13) is substantially the same, e.g. max 1 bar lower, than at the liquid outlet (108). In this way, formation of biphasic fluid flow between the liquid outlet (108) and the inlet (13) is avoided, which contributes to good transport of the urea solution to the tube bundle and distribution thereof over the tubes of tube bundle.

The pool reactor preferably comprises vertical baffles in the shell. Preferably one of the baffles is configured as an overflow weir (110) providing for gas/liquid separation in the shell side space (18).

Generally, in all embodiments of the urea production plant (100), the lower leg portion (7) of the outer first U-shaped tube bundle (5) is preferably connected through (second MP) gas/liquid separation (106), directly or indirectly for urea solution, to a low pressure (LP) dissociator. The LP dissociator is typically comprised in an LP recovery section. The LP urea solution from the LP dissociator is e.g. supplied to an evaporation section. Urea melt from the evaporation section is e.g. supplied to a finishing section where it is solidified into solid urea product, using e.g. fluidized bed granulation or prilling. The urea melt can also be supplied, in part or entirely, as feed to a melamine plant. The MP or LP urea solution can also be purified and used for making Diesel Exhaust Fluid (DEF).

Gas from the second MP gas/liquid separation is e.g. condensed into MP carbamate solution in an MP carbamate condenser, typically in heat exchanging contact with urea solution to be heated. The MP carbamate condenser is for instance a shell-and-tube heat exchanger with MP gas to be condensed in the shell side and urea solution to be heated in the tubes, typically with a vertical tube bundle. The urea solution to be heated is typically urea solution obtained directly or indirectly from the LP dissociator, which is expanded to sub-atmospheric pressure, of typically 0.2-0.5 bara, preferably 0.25-0.35 bara. The heated urea solution is e.g. supplied to the evaporation section. The heat exchanger thereby provides for a combined MP carbamate condenser and a pre-evaporator. Thereby effectively heat is used three times, first for HP stripping, then for MP carbamate dissociation in the HP carbamate condensation apparatus, and finally for heating urea solution and/or water removal in the pre-evaporator; thereby providing advantageously for two heat recovery heat exchanges through a wall without the use of steam as heat transfer fluid. The pre-evaporation and evaporation section are used to reduce the water content of the urea solution typically to give a urea melt with at least 90 wt. % or at least 95 wt. % urea and less than 10 wt. %, or less than 5 wt. %, or less than 2 wt. % water. Thereby the urea melt is suitable for finishing methods such as granulation and prilling.

The evaporation section comprises e.g. a vacuum evaporator operating at less than 0.30 bara or less than 0.10 bara.

Gas from the LP dissociator is typically condensed into LP carbamate solution. These carbamate solutions are typically recycled to the HP carbamate condensation apparatus.

Generally, the MP urea solution from the HP carbamate condensation apparatus according to the invention can processed e.g. in a MP section recirculation section as shown in FIG. 1 of US20150119603A1 and comprising a MP separator, an MP rectifying column and an MP condenser/evaporator.

The invention also provides a urea production process for the production of urea from ammonia and carbon dioxide carried out in a urea production plant (100) according to the invention, the process comprising supplying gas from the HP stripper (102) to the shell side of the HP carbamate condensation apparatus (104) and condensing said gas into carbamate at least in part at said shell side and converting said carbamate at least in part into urea at said shell side, and supplying an MP urea solution also comprising carbamate to the inlet for an MP urea-comprising stream.

The process involves exchanging heat from a high pressure process medium received in the shell side space (18) to the MP urea containing solution, which also contains carbamate, received in the first U-shaped tube bundle (4), thereby decomposing at least a part of said carbamate into $NH_3$ and $CO_2$.

The process also involves providing boiler feed water to the inlet of the second U-shaped tube bundle. Suitable boiler feed water is e.g. steam condensate. Typically, steam is raised in the second tube bundle.

The urea solution from the stripper, in particular from the HP $CO_2$ stripper (102), is e.g. flashed in a flash tank at medium pressure, e.g. 20-30 bar, to give flash vapor and flashed urea solution. More preferably the flash pressure is 23-28 bar, even more preferably 25-28 bar. Flashing refers to adiabatic expansion of the urea solution and separation of the released liquid. The flash tank e.g. has an inlet for liquid, an outlet for gas at the top and an outlet for liquid at the bottom.

The flash vapor is relatively $CO_2$ rich and is supplied, directly or indirectly, to the MP carbamate condenser, to adjust (lower) the $NH_3:CO_2$ molar ratio in the condenser.

The flashed urea solution is optionally further reduced in pressure in the MP pressure range and is supplied to the first U-shaped tube bundle. Preferably, the flashed urea solution is kept at the same pressure and is supplied to the first U-shaped tube bundle. The flashing step allows for only liquid to be sent to the first U-shaped tube bundle thereby contributing to good distribution of liquid over the tubes. This applies to both embodiments using a redistribution chamber (25) and embodiments using a tube sheet (20).

The flash vapor is e.g. condensed in the MP carbamate condenser, optionally after counter-current contacting of the MP urea solution from the second gas/liquid separation step downstream of the first U-shaped tube bundle to provide for advantageously lower $NH_3:CO_2$ molar ratio in a LP carbamate condenser.

Preferably the MP urea solution supplied to the first U-shaped tube bundle is obtained by adiabatic expansion and gas/liquid separation of urea solution from the HP synthesis section to a MP urea solution and the urea solution has a temperature at the inlet that is at least 10° C. lower or at least 20° C. lower than at the outlet of the HP carbamate condensation apparatus.

The urea solution at the inlet of the first tube bundle comprises e.g. 40-60 wt. % urea, 20-30 wt. % water, 10-20 wt. % $NH_3$ and 10-20 wt. % $CO_2$, wherein the amounts for $NH_3$ and $CO_2$ include the respective amounts present as carbamate in the solution. The pressure is e.g. 20-30 bar. The temperature is e.g. 130-150° C.

The liquid phase at the outlet of the first tube bundle, i.e. after gas/liquid separation, comprises e.g. 50-70 wt. % urea, e.g. at least 5 wt. % more than at the inlet (percentage point), and typically comprises 2-7 wt. % $CO_2$ including $CO_2$ present as carbamate, e.g. at least 5 wt. % (percentage point) less $CO_2$ including $CO_2$ present as carbamate than at the inlet.

The amount of the gas phase at the outlet of the first tube bundle corresponds to e.g. 10-20 wt. % of the urea solution at the inlet of the first tube bundle.

Generally, the inventive HP carbamate condensation apparatus (104) can be used in a urea plant (100) and process as shown in US20150119603A1.

Figure 4:
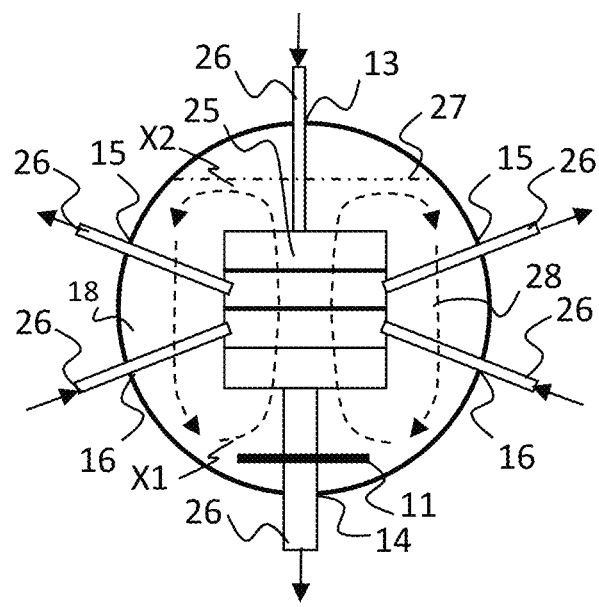
FIG. 4 schematically illustrates a cross section of an example of a HP carbamate condensation apparatus according to the invention.

FIG. 4 schematically illustrates an example HP condensation apparatus (104) according to the invention, more in particular a vertical cross section essentially through point A in FIG. 3. Reference numbers are the same as in FIG. 1 and FIG. 3 unless otherwise specified. The HP carbamate condensation apparatus (104) comprises a redistribution chamber (25) and a duct (26) as discussed hereinbefore. In operation, the tube bundle is submerged in liquid in the shell side space (18) as indicated by the liquid level (27). The flow of the condensed process medium in the shell side space (18) at the vertical cross-section through point B in FIG. 3, i.e. through the reaction zone (103), is indicated by dashed arrows (28). Gas from the first fluid distributor (11) (shown as a vertical cross-section through point B in FIG. 3) causes upward flow in the centre of the vessel and circulating motion. The outlet (14) for MP urea-comprising stream has a larger flow area (diameter) than the inlet (13) for MP urea-comprising stream, as illustrated. In practice, the outlets for steam (15) also have a larger flow area than the inlet for boiler feed water (16) (not shown).

The term "carbamate" as used herein refers to ammonium carbamate as that term in used in the field of urea production.

The term "typical" as used herein indicates features that are frequently used but that are not essential. The phrase "in particular" indicates features that are exemplary and are not essential.

As used herein, for process streams (i.e. not for steam lines), high pressure (HP) is above 100 bar, for instance 120 to 300 bar, typically 150 to 200 bar. Medium pressure (MP) is for example 10 to 70 bar (including intermediate pressure of 30 to 70 bar), in particular 15 to 30 bar, and low pressure (LP) is for example 0 to 10 bar, in particular 1 to 8 bar or 2 to 5 bar. All pressures are bar absolute (bara).

Condensation in a carbamate condenser refers to so-called carbamate condensation, which involves the reaction of $NH_3$ and $CO_2$ into carbamate forming carbamate solution. Carbamate decomposition refers to the dissociation reaction of carbamate into $NH_3$ and $CO_2$.

As used herein, gas with reference to HP process medium includes supercritical fluids.

Preferably the urea production process is carried out in the inventive urea plant. All preferences for the urea production process apply equally for the urea plant. All preferences and details indicted for equipment parts in connection with the urea production process, apply equally for the urea plant.

Example 1

In an example process, the urea solution comprising carbamate at the inlet at the top of the inventive HP carbamate condensation apparatus is about 143° C. and about 25 bar, and at the outlet at the bottom of the HP carbamate condensation apparatus is about 165° C. and 24.5 bar.

Process medium at the shell side, i.e. HP process fluid, is at the bottom about 173° C. and 171° C. at the top (i.e. at the liquid level and at about the height of the upper legs of the outer first U-shaped tube bundle). These points are indicated as X1 respectively X2 in FIG. 4). The first U-shaped tube bundle receives the MP urea solution at the upper legs. In the second U-shaped tube bundle, steam condensate is supplied at the lower legs at about 148° C. and 4.9 bar and steam is released at 4.4 bar and 148° C. along with non-evaporated boiler feed water. The configuration of the flows in the shell and in the two tube bundles contributes to good heat exchange in the HP carbamate condensation apparatus.

The urea solution at the inlet of the first tube bundle comprises 40-60 wt. % urea, 20-30 wt. % water, 10-20 wt. % $NH_3$ and 10-20 wt. % $CO_2$, wherein the amounts for $NH_3$ and $CO_2$ include the respective amounts present as carbamate in the solution. The pressure is 20-30 bar. The temperature is 130-150° C.

The liquid phase at the outlet of the first tube bundle, i.e. after gas/liquid separation, comprises 50-70 wt. % urea, namely at least 5 wt. % more than at the inlet (percentage point), and comprises 2-7 wt. % $CO_2$ including $CO_2$ present as carbamate, e.g. at least 5 wt. % less $CO_2$ including $CO_2$ present as carbamate than at the inlet (percentage point).

The invention claimed is:

1. A high pressure carbamate condensation apparatus comprising a shell-and-tube heat exchanger comprising a shell and a first and a second horizontal U-shaped tube bundle each having an upper leg portion and a lower leg portion connected by a bend portion, a shell side space confined by the shell, a first fluid distributor arranged in the shell side space at a bottom section of the condensation apparatus for distributing a first high pressure gas stream into the shell side space, and an inlet and outlet for a MP urea-comprising stream,
   wherein the first U-shaped tube bundle is arranged around the second U-shaped tube bundle and the upper leg portion of the outer first U-shaped tube bundle is proximally connected to the inlet for the MP urea-comprising stream and the lower leg portion of the outer first U-shaped tube bundle is proximally connected to the outlet for the MP urea-comprising stream and wherein the inner second U-shaped tube bundle is configured for raising steam; wherein the outlet for the MP urea-comprising stream has a larger flow area than the inlet for the MP urea-comprising stream.

2. The high pressure carbamate condensation apparatus according to claim 1, wherein the outlet for the MP urea-comprising stream is provided by two or more outlet nozzles.

3. The high pressure carbamate condensation apparatus according to claim 1, comprising a reaction zone in the shell side space between the bend of the first U-shaped tube bundle and the shell.

4. The high pressure carbamate condensation apparatus according to claim 1, further comprising a second fluid distributor arranged at a bottom section of the condensation apparatus for distributing a second high pressure gas stream into the shell side space.

5. The high pressure carbamate condensation apparatus according to claim 1, wherein said high pressure condensation apparatus comprises a tube sheet, wherein said U-shaped tube bundles are arranged at a first side of said tube sheet and said inlets and outlets are provided by headers arranged at a second side of said tube sheet.

6. The high pressure carbamate condensation apparatus according to claim 1, wherein the apparatus comprises a redistribution chamber, wherein said redistribution chamber comprises a wall for separating HP process medium in the shell side from MP urea stream inside the redistribution chamber, wherein an end of the first U-shaped tube bundle is connected to the redistribution chamber such that said MP urea stream can flow between the first U-shaped tube bundle and said redistribution chamber,
wherein the high pressure carbamate condensation apparatus further comprises a duct extending from the inlet or the outlet for the MP urea stream to said redistribution chamber, such that the MP urea stream can flow between the first U-shaped tube bundle and said inlet or outlet through said redistribution chamber and said duct.

7. The high pressure carbamate condensation apparatus according to claim 6, wherein the duct extending to the redistribution chamber that is connected directly to the upper leg portion of the outer first U-shaped tube bundle is arranged vertically upward.

8. The high pressure carbamate condensation apparatus according to claim 4, wherein the second fluid distributor extends horizontally below the first U-shaped tube bundle.

9. The high pressure carbamate condensation apparatus according to claim 6, wherein the redistribution chamber is located in the shell side space.

10. A urea production plant comprising a high pressure synthesis section comprising a HP stripper, a reaction zone, and a high pressure carbamate condensation apparatus, wherein the high pressure carbamate condensation apparatus comprises a shell-and-tube heat exchanger comprising a shell and a first and a second horizontal U-shaped tube bundle each having an upper leg portion and a lower leg portion connected by a bend portion, a shell side space confined by the shell, a first fluid distributor arranged in the shell side space at a bottom section of the condensation apparatus for distributing a first high pressure gas stream into the shell side space, and an inlet and outlet for a MP urea-comprising stream, wherein the first U-shaped tube bundle is arranged around the second U-shaped tube bundle and the upper leg portion of the outer first U-shaped tube bundle is proximally connected to the inlet for the MP urea-comprising stream and the lower leg portion of the outer first U-shaped tube bundle is proximally connected to the outlet for the MP urea-comprising stream and wherein the inner second U-shaped tube bundle is configured for raising steam,
wherein the high pressure synthesis section, the reaction zone and/or the HP stripper, has a liquid flow connection for urea solution through an expansion device to said inlet for MP urea-comprising stream and to said upper leg portion of the outer first U-shaped tube bundle, wherein the stripper has a gas flow line connected to a gas inlet of the shell side of the condensation apparatus.

11. The urea production plant according to claim 10, wherein the urea production plant comprises a gas/liquid separator for urea solution from the expansion device, which gas/liquid separator is arranged at a vertically higher level of the urea production plant than the inlet for MP urea-comprising stream and the upper leg portion of the outer first U-shaped tube bundle, and has a liquid outlet connected to the inlet for MP urea-comprising stream.

12. The urea production plant according to claim 11, wherein the high pressure carbamate condensation apparatus comprises a redistribution chamber, wherein said redistribution chamber comprises a wall for separating HP process medium in the shell side from MP urea stream inside the redistribution chamber, wherein an end of the first U-shaped tube bundle is connected to the redistribution chamber such that said MP urea stream can flow between the first U-shaped tube bundle and said redistribution chamber,
wherein the high pressure carbamate condensation apparatus further comprises a duct extending from the inlet or the outlet for the MP urea stream to said redistribution chamber, such that the MP urea stream can flow between the first U-shaped tube bundle and said inlet or outlet through said redistribution chamber and said duct, and wherein the duct extends vertically between the redistribution chamber and the inlet for MP urea-comprising stream.

13. The urea production plant according to claim 10 wherein said reaction zone is provided as a vertical urea reactor or as a part of said high pressure carbamate condensation apparatus.

14. The urea production process for the production of urea from ammonia and carbon dioxide carried out in a urea production plant according to claim 10, comprising supplying gas from the HP stripper to the shell side of the HP carbamate condensation apparatus and condensing said gas into carbamate at least in part at said shell side and converting said carbamate at least in part into urea at said shell side, and supplying an MP urea solution also comprising carbamate to said inlet for an MP urea-comprising stream.

15. The urea production process according to claim 14, wherein the MP urea solution is obtained by adiabatic expansion and gas/liquid separation of urea solution from the HP synthesis section to a MP urea solution and has a temperature at the inlet that is at least 10° C. lower than at the outlet.

16. The urea production process according to claim 15, wherein a urea solution liquid column of at least 3 m height is maintained at the inlet for the MP urea-comprising stream.

17. The urea production plant according to claim 11, wherein the gas/liquid separator is a flash vessel.

18. The urea production plant according to claim 12, wherein the redistribution chamber is located in the shell side space.

* * * * *